United States Patent
Mrochen et al.

(10) Patent No.: US 8,753,321 B2
(45) Date of Patent: *Jun. 17, 2014

(54) APPARATUS FOR COUPLING AN ELEMENT TO THE EYE

(75) Inventors: Michael Mrochen, Zürich (CH); Michael Büeler, Zürich (CH); Christof Donitzky, Eschenau (DE); Christian Wüllner, Möhrendorf (DE)

(73) Assignee: Wavelight AG, Erlangen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/435,693

(22) Filed: Mar. 30, 2012

(65) Prior Publication Data
US 2012/0191077 A1    Jul. 26, 2012

Related U.S. Application Data

(63) Continuation of application No. 12/531,217, filed as application No. PCT/EP2008/002014 on Mar. 13, 2008, now Pat. No. 8,475,433.

(30) Foreign Application Priority Data

Mar. 14, 2007    (EP) .................................... 07005280

(51) Int. Cl.
*A61F 9/009* (2006.01)
*A61F 9/008* (2006.01)

(52) U.S. Cl.
CPC ................ *A61F 9/009* (2013.01); *A61F 9/008* (2013.01)
USPC ............................................. 604/294; 606/5

(58) Field of Classification Search
CPC ...................................................... A61F 9/009
USPC ................................ 604/294, 541, 297; 606/5
See application file for complete search history.

(56) References Cited

U.S. PATENT DOCUMENTS 4,546,773 A    10/1985   Kremer et al.
4,662,370 A  *  5/1987   Hoffmann et al. ............ 606/166
(Continued)

FOREIGN PATENT DOCUMENTS

EP    0327693    8/1989
EP    0993814    4/2000
(Continued)

OTHER PUBLICATIONS

Japanese Patent Office, Office Action for Japanese Application No. 2012-288583, Nov. 26, 2013, 16 pages.

*Primary Examiner* — Melanie Hand
*Assistant Examiner* — Paula Craig
(74) *Attorney, Agent, or Firm* — Haynes and Boone, LLP

(57) ABSTRACT

The invention relates to methods of treating an eye that include coupling a suction ring to the eye and introducing a liquid into an interior chamber of a container element coupled to the suction ring. The container element is also coupled to a focusing lens of a laser system such that only the liquid within the interior chamber is positioned between the focusing lens of the laser system and an outer surface of the eye. In some embodiments, the suction ring has a first suction region that is designed to suck the suction ring onto an eye and a second suction region that is designed to couple the suction ring to the container element.

14 Claims, 4 Drawing Sheets

(56) References Cited

U.S. PATENT DOCUMENTS

Figure 1:
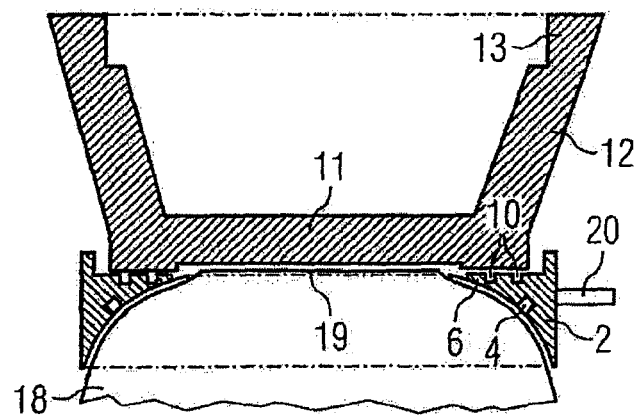

| | | | |
|---|---|---|---|
| 4,669,466 A | 6/1987 | L'Esperance | |
| 4,798,599 A * | 1/1989 | Thomas | 604/290 |
| 5,032,020 A | 7/1991 | Robert | |
| 5,112,328 A * | 5/1992 | Taboada et al. | 606/4 |
| 5,133,708 A | 7/1992 | Smith | |
| 5,133,726 A * | 7/1992 | Ruiz et al. | 606/166 |
| 5,215,104 A * | 6/1993 | Steinert | 128/898 |
| 5,336,215 A | 8/1994 | Hsueh et al. | |
| 5,496,339 A * | 3/1996 | Koepnick | 606/166 |
| 5,549,632 A | 8/1996 | Lai | |
| 5,586,980 A * | 12/1996 | Kremer et al. | 606/4 |
| 5,616,139 A | 4/1997 | Okamoto | |
| 5,624,456 A * | 4/1997 | Hellenkamp | 606/166 |
| 5,643,299 A * | 7/1997 | Bair | 606/166 |
| 5,741,245 A * | 4/1998 | Cozean et al. | 606/5 |
| 5,828,454 A | 10/1998 | Gust | |
| 6,099,522 A | 8/2000 | Knopp | |
| 6,126,668 A | 10/2000 | Bair et al. | |
| 6,165,189 A * | 12/2000 | Ziemer | 606/166 |
| 6,342,053 B1 | 1/2002 | Berry | |
| 6,344,040 B1 | 2/2002 | Juhasz et al. | |
| 6,497,700 B1 * | 12/2002 | LaHaye | 606/4 |
| 6,569,153 B1 | 5/2003 | LaHaye | |
| 7,141,047 B2 | 11/2006 | John | |
| 8,475,433 B2 * | 7/2013 | Mrochen et al. | 604/541 |
| 2002/0049428 A1 | 4/2002 | Bruce | |
| 2003/0153904 A1 * | 8/2003 | Patel | 606/5 |
| 2003/0158543 A1 | 8/2003 | Van Saarloos | |
| 2005/0192562 A1 | 9/2005 | Loesel et al. | |
| 2006/0192921 A1 | 8/2006 | Loesel et al. | |
| 2007/0016234 A1 | 1/2007 | Daxer | |
| 2007/0093795 A1 | 4/2007 | Melcher et al. | |
| 2007/0237620 A1 | 10/2007 | Muhlhoff et al. | |
| 2008/0033408 A1 | 2/2008 | Bueler et al. | |
| 2009/0137989 A1 | 5/2009 | Kataoka | |
| 2010/0274228 A1 * | 10/2010 | Mrochen et al. | 604/541 |
| 2011/0009851 A1 | 1/2011 | Donitzky et al. | |
| 2012/0191077 A1 | 7/2012 | Mrochen et al. | |

FOREIGN PATENT DOCUMENTS

| | | |
|---|---|---|
| EP | 1199055 | 4/2002 |
| JP | 5165760 B2 | 3/2013 |
| WO | WO0041660 | 7/2000 |
| WO | WO/03001991 | 1/2003 |
| WO | WO/03002008 | 1/2003 |
| WO | WO/2004096106 | 11/2004 |
| WO | WO/2005048895 | 6/2005 |
| WO | WO2006/090217 A1 | 8/2006 |
| WO | WO/2006090217 | 8/2006 |
| WO | WO2006/121066 A1 | 11/2006 |
| WO | WO/2006121066 | 11/2006 |

* cited by examiner

APPARATUS FOR COUPLING AN ELEMENT TO THE EYE

CROSS-REFERENCE TO RELATED APPLICATIONS

This patent application is a continuation of U.S. patent application Ser. No. 12/531,217 filed on Apr. 29, 2010, which is a United States national phase application of co-pending international patent application number PCT/EP2008/002014, filed Mar. 13, 2008, which claims the benefit of European patent application number EP 07005280.8, filed Mar. 14, 2007, each of which is hereby incorporated by reference in its entirety.

The invention relates to a suction ring for ophthalmic surgery, with a first suction region which is designed to suck the suction ring onto an eye, and with a second suction region which is designed to aspirate a functional element.

Pulsed laser radiation is used in eye surgery, for example, for the purpose of making incisions in the cornea or for the purpose of resecting (ablating) tissue out of the cornea. The radiated laser radiation brings about a photodisruptive or photoablative process in the corneal tissue, which results in the severing of tissue or in the removal of tissue material. Such treatments of the cornea take place, for example, within the scope of refractive processes for lessening or totally eliminating visual defects of the eye, in which processes the cornea is reshaped and, by this means, its refractive properties are changed.

The dominant refractive process of corneal surgery is so-called LASIK (laser in-situ keratomileusis). In this case a small cover, which remains connected to the cornea by a part of its edge, is cut out of the cornea either mechanically (by means of an oscillating cutting blade in a so-called microkeratome) or optically (by means of laser radiation, e.g. by means of femtosecond laser systems). Subsequently this cover, which ordinarily is also designated as a flap, is folded aside, as a result of which the underlying stroma becomes accessible. Stromal tissue is then resected with laser radiation in accordance with an ablation profile ascertained for the respective patient. The cover is then folded back again, as a result of which the wound can heal relatively quickly.

For a precise coupling of the laser radiation into the eye, in this case it is known to fix the eye by means of a fixation device which is aspirated to the eye by partial vacuum. The fixation device may exhibit a glass serving as coupling element for the laser radiation. Fixation devices of such a type are also designated as suction rings.

As soon as the suction ring has been arranged on the eye of a patient and fixed to the eye by means of a partial vacuum, energy is introduced into the interior of the cornea by means of pulses of a femtosecond laser. As a result, an incision is produced in the cornea, the flap can be folded upwards, and correction of the visual defect can be effected by a defined resection of exposed corneal tissue.

Suction rings are known as such to a person skilled in the art; for example, U.S. Pat. No. 5,336,215 and U.S. Pat. No. 5,549,632 disclose suction rings which in their peripheral region include openings, taking the form of suction regions, for the purpose of aspirating onto an eye. EP 0 993 814 A1 and U.S. Pat. No. 6,342,053 B1 disclose suction rings in which a partial vacuum is generated in the region of an applanation surface, so that the cornea of the eye rests thereon. U.S. Pat. No. 6,344,040 B1 presents a suction ring in which a partial vacuum is generated in the region of an applanation surface, the suction ring further including a probe which in operation pierces the cornea and extracts the gases and particles arising during the photodisruptive process by means of suction. WO 03/002008 A1 discloses a suction ring with an aspiration region formed on the periphery of the suction ring, a conical lens mount with a lens being arranged on the suction ring by means of a forceps-like gripper.

WO 00/41660 A1 describes a device for carrying out an operation on the eye, with a first annular, fixed vacuum region and with a central, mobile vacuum region. In operation the mobile vacuum region is located above the cornea to be operated on and is able to give said cornea a desired shape for the operation. The second vacuum region may include a plurality of elements, so that its shape and consequently the contour of the cornea can be changed during the operation.

WO 03/001991 A1 discloses a contact lens with a plurality of strain gauges for measuring the intraocular pressure. The supply of power to the strain gauges and the communication are effected in non-contacting manner.

The suction rings pertaining to the state of the art include applanation elements which are coupled with the suction ring by means of elaborate mechanical appliances.

The intraocular pressure acting in the course of aspiration of the suction ring can result in damage, and hitherto has not been known to the operating surgeon during the treatment of an eye. Furthermore, the positioning of the suction ring, for example with respect to a femtosecond laser system, is critical, and under certain circumstances can lead to treatment errors or injuries as a result of displacement of the treatment couch. The position of the suction ring and of the eye, in particular with respect to a treatment couch and the laser beam, is relevant to safety. A mechanical force that acts on the eye during the laser treatment is influenced under certain circumstances by the mechanical forces arising in the course of a movement of the head, and can lead to an injury. In the course of the treatment the water content and/or the biomechanical properties of the cornea can be important for the outcome of the treatment. The transparency of the cornea is likewise important for the treatment with laser pulses in order to improve the safety of the operation.

It is an object of the invention to extend the possible applications of a suction ring.

This object is achieved by means of an eye-suction device that includes a first suction region, which in operation is designed to suck the eye-suction device onto an eye, and a functional element. The eye-suction device or the functional element includes a second suction region, which in operation is designed to suck the functional element onto the eye-suction device. The second suction region may be arranged on the functional element and/or on the eye-suction device. Before, during and/or after the operation the operating surgeon can couple arbitrary requisite elements with the eye-suction device in simple manner, without intricate, time-consuming working steps being required for this, as a result of which the success of the treatment is ensured. Furthermore, prior to a surgical procedure the operating surgeon can select the appropriate functional element more simply and couple it with the eye-suction device. The term 'eye-suction device' encompasses any device that is designed to be aspirated onto an eye, for example a so-called suction ring. The suction region may be formed, for example, by an opening or a recess in which a partial vacuum prevails in operation. The partial vacuum may be generated, for example, by a suction pump connected to the suction region. However, it is also possible that the partial vacuum arises automatically when coupling the functional element onto the eye-suction device or when coupling the eye-suction device onto the eye, by, for example, a sealing lip being displaced, so that an evacuated suction region arises.

The functional element may be an optical element, for example a glass or a lens, through which the laser radiation is introduced into the cornea. Furthermore, the optical element may be a so-called applanation lens or applanation plate. The functional element may be a retaining element which is designed so that further elements can be arranged thereon. An optical element may be arranged on the retaining element. As a result, a particularly versatile eye-suction device arises, since the optical element can be exchanged very easily. An applanation element may also be arranged on the retaining element, in which case the optical element arranged on the retaining element may also take the form of an applanation lens. The functional element may be designed to be coupled with an optical device. The optical device may be a laser system, for example a femtosecond laser system, with associated optics. The functional element may also be a mechanical microkeratome mentioned in the introduction. The functional element may also be an adapting cone, with which the suction ring is coupled onto an ophthalmic device. The functional element may have been provided both for retaining the applanation element and for coupling the eye-suction device with the ophthalmic device. In the following, a functional element of such a type will be designated as a retaining element.

The eye-suction device may include a first partial-vacuum feed, which is connected to the first suction region, and a second partial-vacuum feed, which is connected to the second suction region. The partial-vacuum feeds can be connected to one or more suction pumps. In operation a partial vacuum may prevail in the first partial-vacuum feed that is different from that in the second partial-vacuum feed, as a result of which different partial vacuums arise in the first and second suction regions. As a result, it is possible to couple the functional element securely with the eye-suction device without such a high partial vacuum being generated in the first suction region that the eye could be injured.

The eye-suction device may be designed in such a manner that in operation at least one region of the cornea of an eye rests against the functional element and/or against an element arranged thereon. As a result, an exact fixation of the cornea arises, ensuring a safe surgical procedure. The eye-suction device may include a third suction region which in operation is in fluidic communication with the surface of the functional element and/or with the surface of the element attached thereto, against which the cornea of the eye rests in operation. As a result, the cornea is fixed in its position particularly well, since the region between the cornea and the functional element or an element arranged on the retaining element is evacuated or is subject to a partial vacuum. Furthermore, it is possible to set the partial vacuum prevailing in the region between the cornea and the functional element and/or an element arranged thereon independently of the partial vacuum in the first and second suction regions. As a result, the risk of injury is minimised and/or the comfort of treatment for a patient is increased, since the force with which the eye-suction device is sucked onto the eye may differ from the force with which the cornea is sucked onto the functional element and/or onto an element arranged thereon. In addition, a particularly safe eye-suction device also arises, which exhibits a redundancy, since two partial-vacuum systems are used in order, on the one hand, to fix the eye-suction device to the eye and, on the other hand, to fix the cornea to a functional element and/or to an element arranged thereon. The eye-suction device may be formed elastically on the first, second and/or third suction region.

In a simplified embodiment the third partial-vacuum feed may be in fluidic communication with the first or second partial-vacuum feed.

The optical element may be an applanation element. The applanation element may be attached to the eye-suction device. After an operation in which it has been exposed to the laser radiation, the applanation element has to be exchanged. The eye-suction device may include an applanation element inseparably attached thereto in operation. The applanation element is consequently integrated into the eye-suction device. The eye-suction device can be made available with the applanation element inseparably attached thereto in operation in the form of a sterile disposable article. As a result, a more cost-effective eye-suction device can be obtained. Furthermore, with an eye-suction device of such a type the mechanical tolerance chain can be reduced to the applanation element and to the aspirated, re-usable retaining element, which is also designated as an adapting cone. By virtue of the reduced tolerance chain, the outcome of the treatment is improved.

The functional element may take the form of a container element which includes a first axial end, which in operation is aspirated by the second suction region of the eye-suction device, a second axial end, which is opposed to the first end, and a wall which extends from the first axial end to the second axial end. The container element may be open at its first and second axial ends and may be closed around the axial direction by the wall, and an optical element may be arranged at the second axial end. The wall may exhibit a first opening, through which a fluid can enter, and a second opening, through which a fluid can emerge. The optical element may be a focusing lens for a laser beam. By reason of the container element, the focusing lens has a fixed spacing from the cornea, as a result of which a safe treatment is guaranteed.

If a fluid is introduced through the first opening, a film of moisture, which guarantees a particularly good sealing of the first suction region, is located in the neighbourhood of the first suction region, as a result of which the eye-suction device is coupled onto the eye particularly securely. The higher the viscosity of the liquid, the better the additional sealing effect.

The container element may be filled with a fluid, the refractive index of which corresponds approximately to the refractive index of the cornea. As a result, no optical aberration of the light arises at the transition to the cornea, as a result of which a good focusability of the laser beam and a high optical quality of the laser beam are guaranteed. The fluid may exhibit a refractive index $\eta_{fluid}$ from approximately 1.35 to approximately 1.40, preferentially from approximately 1.36 to 1.38, most preferentially of approximately 1.37. The refractive index $\eta_{cornea}$ of the cornea amounts to approximately 1.376, and if the refractive index of the fluid exhibits a similar refractive index the quality and/or the intensity of a light beam or of a laser beam at the transition from the optical eye-contact element to the cornea is/are not diminished.

The reflection losses R are calculated as follows:

$$R = \left(\frac{\eta_{cornea} - \eta_{fluid}}{\eta_{cornea} + \eta_{fluid}}\right)^2;$$

Given $\eta_{cornea} \approx \eta_{fluid}$ it follows that almost no reflection losses arise.

Via the second opening, air is able to escape in the course of filling of the container element.

Furthermore, in this embodiment no applanation element is required, as a result of which the ocular pressure is not increased during the treatment. Furthermore, no aberration, for example a wavefront error, can arise by reason of a spherical or aspherical applanation as in the case where an applanation element is employed. As a result, a laser radiation with a low wavefront error is obtained, which is advantageous with regard to the focusing, since the focal positions scatter less intensely and the laser radiation is concentrated onto a smaller region of focus.

The applicant expressly reserves the right to make a separate application for protection for the previously described aspect with regard to an eye-suction device with a container element, wherein the eye-suction device and the container element may also be integrally formed or may be coupled with one another not only by means of partial vacuum but also mechanically, for example positively or frictionally.

The eye-suction device may include at least one measuring means. The expression 'measuring means' in this context also encompasses the qualitative and/or quantitative determination or ascertainment of a geometrical, physical and/or chemical quantity. The eye-suction device may include a plurality of measuring means. The functional element may include at least one measuring means.

Since the known suction ring has to be frequently disinfected, sterilised and exchanged, and the eye is a particularly sensitive organ, a person skilled in the art was hitherto deterred from arranging more elaborate measuring means on a suction ring or from creating more elaborate measuring means which are arranged on or in a suction ring in direct proximity to the eye, particularly since during the operation a part of the very sensitive cornea is folded upwards.

At least one of the measuring means of the eye-suction device may be designed to carry out a measurement with respect to a property of the eye. The measuring means may be designed to determine the intraocular pressure, in which case the intraocular pressure can be ascertained, for example, by means of tactile, mechanical, acoustic and optical processes, in particular also resonance processes.

At least one measuring means of the eye-suction device may be designed to measure properties of the cornea of the eye. The measuring means for measuring the properties of the cornea of the eye may measure the water content of the cornea, a biomechanical property of the cornea, and/or the transparency of the cornea. The water content may be determined, for example, by means of an optical spectrometer; the biomechanical properties of the cornea may be determined, for example, by mechanical spectroscopic processes; and the transparency of the cornea may be determined by scattering of light.

The eye-suction device may include a measuring means for measuring a quantity acting on the eye. The measuring means for measuring a quantity acting on the eye may measure a force acting on the eye. For this purpose, pressure sensors, for example piezoelectric pressure sensors, or force sensors may be integrated into the suction ring. Furthermore, it is possible to use microelectromechanical systems (MEM systems) which, for example, are arranged on the optical element via which the laser radiation is introduced.

The eye-suction device may include at least one measuring means for measuring a property of the eye and/or of the eye-suction device with respect to the environment. The measuring means for measuring a property of the eye and/or of the eye-suction device with respect to the environment may measure, for example, the position of the eye and/or of the eye-suction device in space. The means for measuring the property of the eye and/or of the suction ring in relation to the environment may be designed to interact with positioning means for a treatment couch and/or with positioning means for laser radiation. As a result, it can be ensured that the eye is always located in the correct position and the laser radiation impinges on the cornea of the eye at the correct position and at the correct angle. The measurement of the position of the eye and/or of the suction ring may be based on a mechanical, high-frequency-based, acoustic or (three-dimensional) optical position detection. The measuring means may be arranged on a functional element which is sucked onto the eye-suction device.

The measuring means may be designed to transmit ascertained measurement data. The measurement data may be transmitted inductively, via a cable, via an optical interface or via an electromagnetic interface. The measuring means may include a battery, may be supplied with current inductively or may be supplied with current via a supply line. The measuring means may further include a communications device. For example, the measuring means may take the form of a transponder, so that an inductive or electromagnetic excitation is effected from the outside and the communications device of the measuring means transmits the ascertained measured values inductively or electromagnetically. The applicant expressly reserves the right to claim protection separately for an eye-suction ring or an eye-suction device with a measuring device, without it being necessary that a functional element be aspirated onto the suction ring.

Figure 2A:
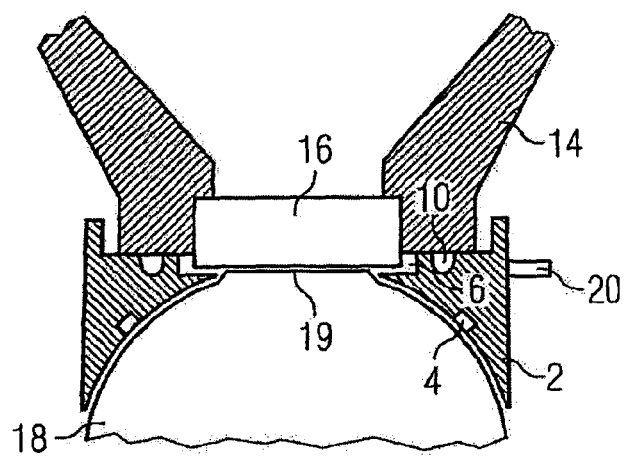
Figure 2B:
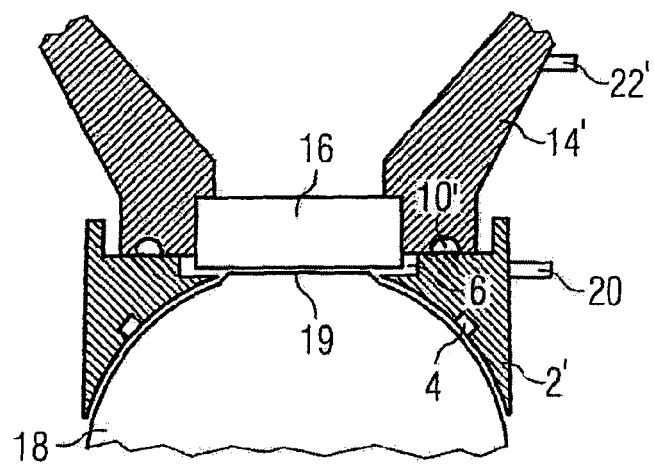
Figure 3:
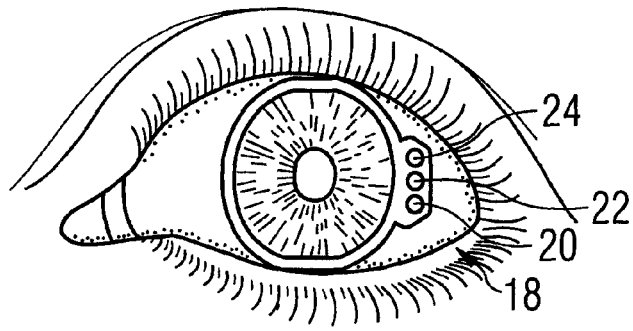
Figure 4:
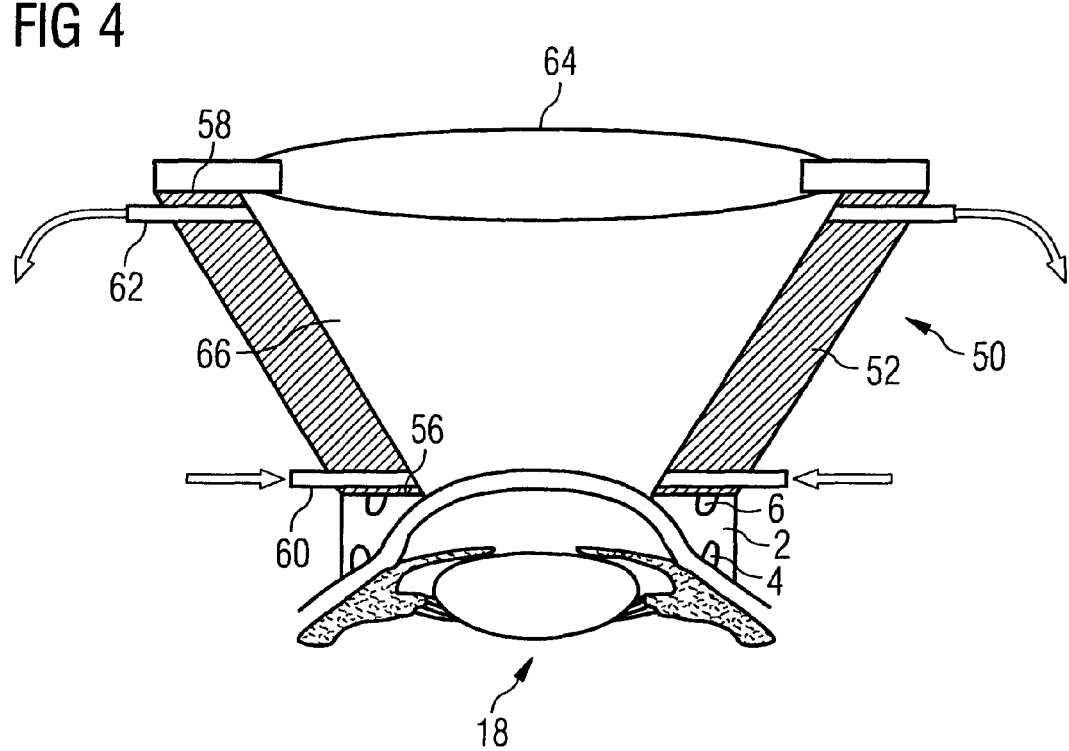
Figure 5:
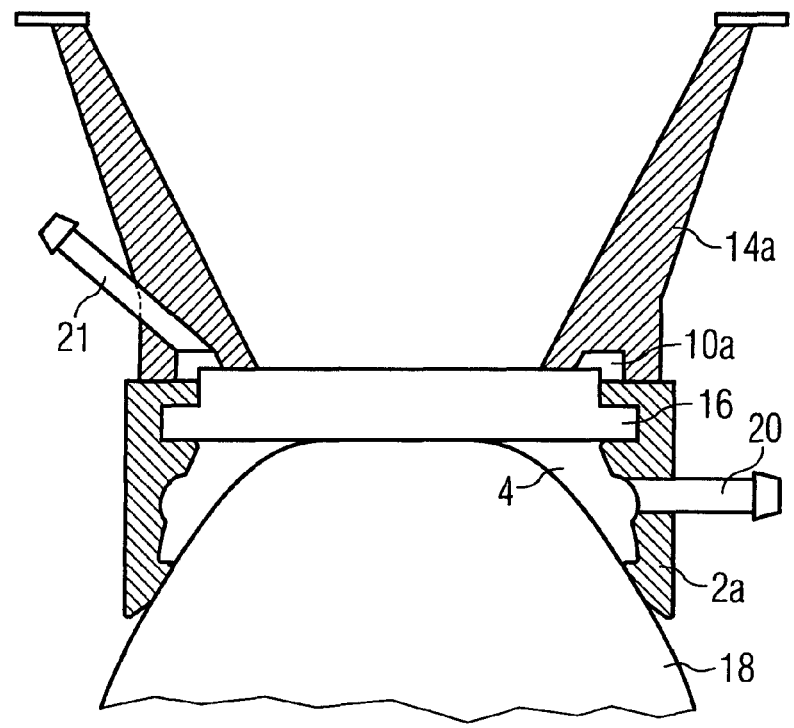
Figure 6:
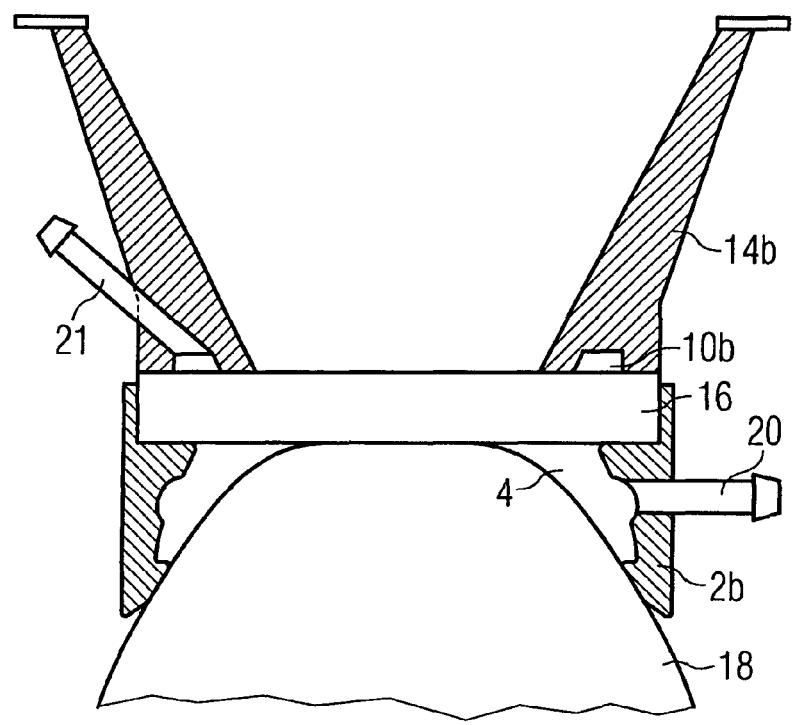
Figure 7:
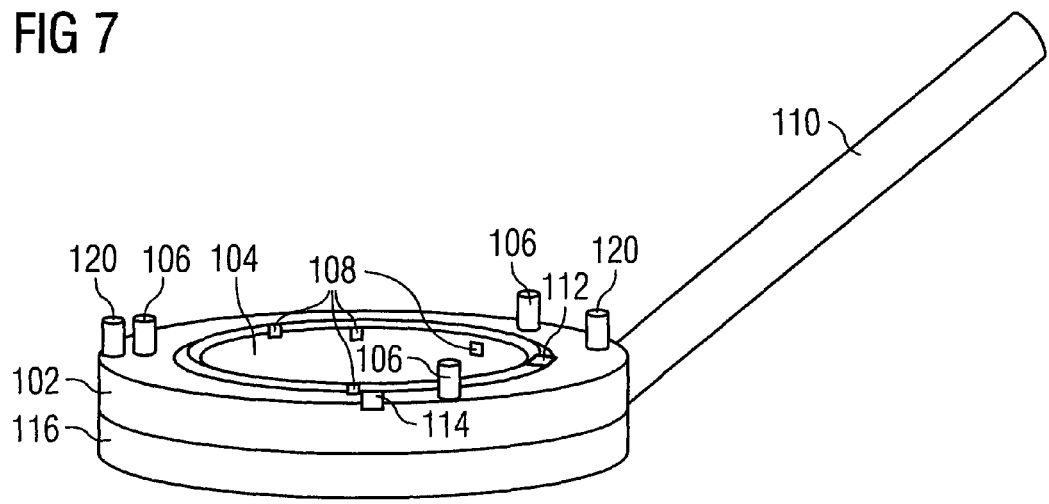
Figure 8:
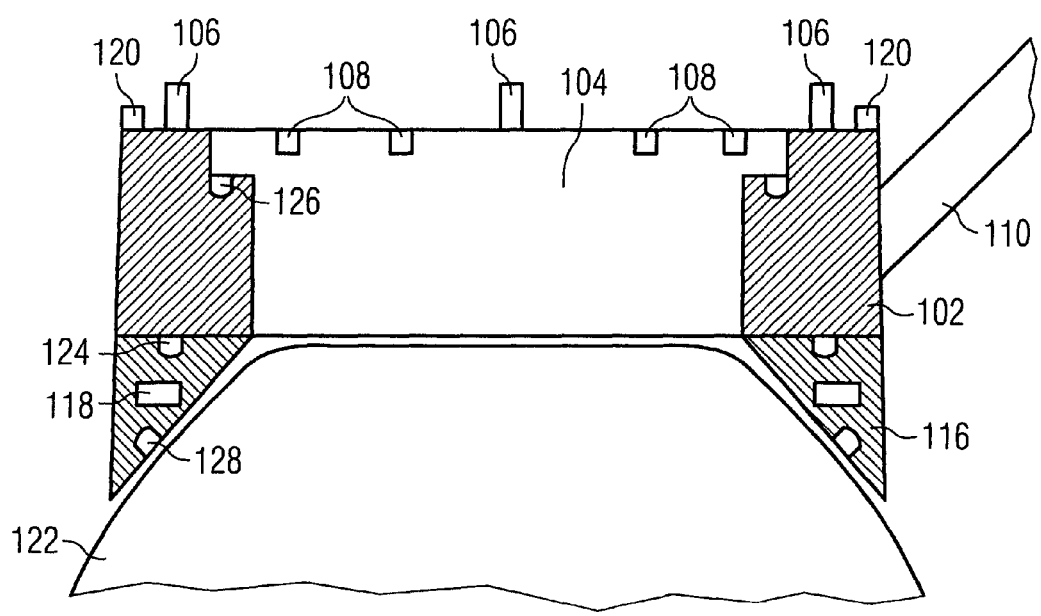

The invention will be elucidated in more detail in the following on the basis of the accompanying drawings. Represented are:

FIG. 1: a schematic section, not true to scale, through a first embodiment of the invention;

FIG. 2a: a schematic section, not true to scale, through a second embodiment of the invention;

FIG. 2b: a schematic section, not true to scale, through a third embodiment of the invention, in which the second suction region is located on the functional element;

FIG. 3: a schematic front view of the invention;

FIG. 4: a schematic view, not true to scale, of a fourth embodiment of the invention, in which a fluid is located between a focusing lens and the cornea during the treatment;

FIG. 5: a schematic view, not true to scale, of a fifth embodiment of the invention, in which an applanation element is attached to the eye-suction device;

FIG. 6: a schematic view, not true to scale, of a sixth embodiment of the invention, in which an applanation element is attached to the eye-suction device;

FIG. 7: a perspective view, not true to scale, of a seventh embodiment of the invention, which includes an eye-suction device with a measuring device; and FIG. 8: a schematic section, not true to scale, through the seventh embodiment of the invention.

FIG. 1 shows an eye-suction device 2 with a first suction region 4, which in operation is designed to suck the eye-suction device 2 onto an eye 18, and with a second suction region 10, which in operation is designed to aspirate a functional element 12. The functional element 12 includes an optical element 11 which takes the form of a lens or plate 11. Furthermore, the functional element 12 includes a connection region 13 with which the functional element can be coupled onto an optical device (not shown) of a laser system, for example a femtosecond laser system.

The eye-suction device further includes a third suction region which is in fluidic communication with the space between the functional element 12 and the cornea 19 of an eye 18 and at least partly evacuates said space, so that at least a part of the cornea rests against the functional element 12. The region against which the cornea 19 rests may take the form of an applanation lens or applanation plate 11. The eye-suction device includes a plurality of partial-vacuum feeds 20, 22, 24

(in FIG. 1 only one is discernible) which are connected to a suction pump or which are each connected to a suction pump or to a suction pump with three separate control devices or three separate control valves. As a result, a different partial vacuum can be generated in the first suction region 4, in the second suction region 10 and in the third suction region 6. In the second suction region 10 a high partial vacuum can be set, in order that the functional element 12 is firmly arranged on the eye-suction device. In the first suction region 4 and/or in the third suction region 6 a lower partial vacuum can be set, in order that the eye 18 is not injured. Furthermore, prior to the operation the operating surgeon may apply a partial vacuum merely in the second suction region 10, in order to arrange the functional element 12 on the eye-suction device 2. In the course of the positioning of the eye-suction device 2 on the eye 18 of the patient a partial vacuum can be generated in the first suction region 4, in order to arrange the eye-suction device 2 securely on the eye 18. Finally, a partial vacuum can be generated in the third suction region 6, in order that the cornea 19 of the eye 18 is securely arranged on the functional element 12. However, it is also conceivable firstly to arrange the eye-suction device 2 on the eye 18 and subsequently to generate a vacuum in the second suction region 10, in order to arrange the functional element 12.

The eye-suction device according to the invention avoids an injury to the eye, since in the first suction region 4 a partial vacuum can be set that is different from that in the second suction region 10 and/or in the third suction region 6. Furthermore, the present invention creates a redundancy, since the eye-suction device is held on the eye both by the first suction region 4 and by the third suction region 6.

The first suction region 4 takes the form of a peripheral groove in the eye-suction device. However, other configurations are also possible, for example a plurality of peripheral grooves, one or more peripheral or non-peripheral indentations or a plurality of openings. The second suction region 10 is formed by two peripheral grooves in the form of a circle on the front side or upper side of the eye-suction device. Here too, the configurations previously described with respect to the first suction region are possible. The third suction region 6 in the first embodiment is located in the transition region from the eye-suction device 2 to the functional element 12. As a result, it can be ensured that a part of the cornea 19 is sucked onto the surface of the functional element 12.

The functional element 12 can be simply exchanged, without special tools and/or elaborate operating steps being required for this. In operation the functional element 12 can simply be replaced by another which, for example, includes another optical element 11, applanation element 11 and/or another connection region 13.

FIG. 2a shows a second embodiment of the invention, wherein identical reference symbols designate identical elements. With respect to the configuration of the first, second and third suction regions as well as the partial-vacuum feeds, reference is made to the description of the embodiment according to FIG. 1.

In contrast to the embodiment according to FIG. 1, in the embodiment according to FIG. 2a a retaining element 14 is arranged on the eye-suction device 2 by means of a partial vacuum in the second suction region 10. The retaining element 14 may be any element on which or to which further elements can be arranged or attached. The retaining element 14 includes on its region facing towards the eye-suction device 2 a peripheral recess in the form of a circle, in which an optical element 16 is arranged. The optical element 16 may take the form of an applanation element or an applanation lens. The retaining element 14 also includes a connection region (not shown) with which the retaining element can be coupled with the optics of a laser system.

By virtue of the partial vacuum in the third suction region 6 the cornea 19 is sucked onto the optical element 16 arranged on the retaining element 14.

FIG. 2b shows a third embodiment of the invention, which resembles the second embodiment. In contrast to the second embodiment, the eye-suction device 2' in the third embodiment does not include a second suction region. The second suction region 10' is arranged in the functional element 14'. Via the second partial-vacuum feed 22' a partial vacuum is generated in the second suction region 10'. The remaining configurations of the eye-suction device 2' and of the functional element 14' correspond to the configurations of the eye-suction device 2 and of the functional element 14 of the second embodiment.

FIG. 3 shows a front view of the suction device according to the invention without mounted functional element in operation.

The eye-suction device includes a first partial-vacuum feed 20 which is connected to the first suction region, a second partial-vacuum feed 22 which is connected to the second suction region, and a third partial-vacuum feed 24 which is connected to the third suction region. The eye-suction device does not have to be substantially circular. It may also take the form, for example, of an elliptical ring or polygonal ring.

FIG. 4 shows a fourth embodiment of a suction ring 2 according to the invention, in which a fluid is located between a focusing lens 64 and the cornea of the eye 18 during the treatment of the eye 18. With the aid of a first partial-vacuum region 4 the eye-suction device 2 is coupled onto the eye 18, for example onto the sclera or the limbus. The region of the eye-suction device 2 that touches the eye 18 is modelled on the anatomical shape of the eye 18 in this region, so that the ocular pressure is not increased or is only slightly increased. However, the eye-suction device 2 and the elements arranged thereon do not touch and/or cover the eye 18 in the region of the cornea to be treated, as a result of which a numerical aperture of approximately 10 mm arises.

The eye-suction device 2 includes a first suction region 4 which aspirates a container element 50 at its first axial end 56. Located opposite the first axial end 56 of the container element 50 is a second axial end 58, on which a focusing lens 64 may be arranged. A wall 52 extends from the first axial end 56 to the second axial end 58 of the container element 50 and around the longitudinal axis of the container element 50 in the axial direction. The container element is consequently closed laterally by the wall 52, upwardly by the focusing lens 64, and downwardly by the cornea of the eye 18.

The wall 52 exhibits a first opening 60, through which a fluid can be supplied, and a second opening 62, through which a fluid can be discharged. If a fluid is supplied through the first opening 60, the air in the interior 66 of the container element escapes through the second opening 62. The fluid supplied to the interior 66 of the container element exhibits a refractive index $\eta$ that is preferentially approximately similar to or the same as that of the cornea, the refractive index $\eta_{cornea}$ of which amounts to approximately 1.376. But it is also possible to use water, the refractive index $\eta_{water}$ of which amounts to approximately 1.333. By virtue of the adaptation of the refractive indices, no optical aberration of the light arises at the transition to the cornea, as a result of which a good focusability of the laser beam and a high optical quality of the laser beam are guaranteed.

If a film of moisture is located in the neighbourhood of the first suction region 4, a particularly good sealing of the first suction region 4, as previously mentioned, is guaranteed, as a result of which the eye-suction device is coupled onto the eye particularly securely. The higher the viscosity of the liquid, the better the additional sealing effect.

Furthermore, as previously mentioned, in this embodiment no applanation element is required, which has the result that the ocular pressure is not increased during the treatment. Furthermore, no aberration, for example a wavefront error, can arise by reason of a spherical or aspherical applanation as in the case where an applanation element is employed. Consequently a laser radiation with a low wavefront error is obtained, which is advantageous with regard to the focusing, since the focal positions scatter less intensely and the laser radiation is concentrated onto a smaller region of focus.

The container element 50 and the eye-suction device 2 may be integrally formed or may be positively or frictionally connected to one another.

FIGS. 5 and 6 show the fifth and sixth embodiments of the invention. The optical element 16 is an applanation element. The applanation element 16 is attached to the eye-suction device 2a, 2b. As previously mentioned, the applanation element 16 has to be exchanged after an operation in which it has been exposed to the laser radiation. The eye-suction device 2a, 2b can be made available with the applanation element 16 attached thereto in the form of a sterile disposable article. As a result, a more cost-effective eye-suction device can be obtained. Furthermore, with an eye-suction device of such a type the mechanical tolerance chain can be reduced to the applanation element 16 and the aspirated, re-usable retaining element 14a, 14b, which is also designated as an adapting cone. By virtue of the reduced tolerance chain the outcome of the treatment is improved.

By virtue of the first partial-vacuum feed 20, a partial vacuum is generated in the first suction region 4, as previously described, so that the eye-suction device 2a, 2b is held on the eye 18. A second partial-vacuum feed 21 generates a second partial vacuum 10a, 10b in the second suction region 10a, 10b, so that the retaining element or the adapting cone 14a, 14b is held securely on the applanation element 16.

In the fifth embodiment according to FIG. 5 the retaining element or the adapting cone 14a touches both the applanation element 16 and the eye-suction device 2a. In this embodiment of the eye-suction device 2a the edge of the applanation element 16 is totally surrounded by the eye-suction device.

In the sixth embodiment according to FIG. 6 the retaining element or the adapting cone 14b touches merely the applanation element 16 and not the eye-suction device 2b. In this embodiment of the eye-suction device 2b the applanation element 16 is able to rest on the eye-suction device 2b only with its lower edge. It may be fastened additionally, for example by means of an adhesive. Also in this embodiment it is possible that the eye-suction device 2b totally surrounds the applanation element 16, so that no adhesive is required. In this case, on its side facing towards the applanation element 16 the retaining element 14b has to exhibit a smaller diameter than the applanation element.

FIGS. 7 and 8 show a seventh embodiment of the invention, which includes an eye-suction device 116, a retaining element 102, an applanation element 104, a supply device 110 with at least one partial-vacuum line and also with a power supply and with a signal connection for at least one measuring means. On the underside of the eye-suction device 116 there is located a first suction region 128 with which the eye-suction device 116 is fixed in relation to the eye 122. The eye-suction device 116 is able to fix the retaining element 102 via a second suction region 124 in which a partial vacuum prevails. The retaining element 102 fixes the applanation element 104 via a third, optional suction region 126. By virtue of the applanation element 104, the radiation of a laser system (not shown), for example a femtosecond laser system, is coupled in. The applanation element may also take the form of a lens. At its lower end the applanation element 104 rests against the cornea of the eye 122, as a result of which the position of the cornea is fixed.

On the upper side of the retaining element 102 there are formed a plurality of mechanical guides 106 for coupling the beam path of the laser and/or a closure mechanism. The mechanical guides 106 may include a force sensor (not represented). Furthermore, the force sensor may be arranged on the mechanical guides, the optics of the laser in this case being coupled to the force sensors. The force sensor may be, for example, a piezoelectric sensor, or it may have been constructed by means of strain gauges.

On the applanation element 104 there may be arranged measuring means for measuring the intraocular pressure. The measuring means may be provided by microelectro-mechanical systems (MEM systems). At the edge of the applanation element 104 there are located a plurality of fibre sensors 108 for implementing a spectroscopic process, for example in the near-infrared region, and/or for implementing a process for determining the scattering of light. With these fibre sensors, properties of the cornea, for example the water content thereof, can be determined. By virtue of the determination of the scattering of light, the transparency of the cornea can also be determined. In the fifth embodiment, however, a separate transparency sensor 114 is provided which, for example by determination of the scattering of light by the cornea, ascertains the transparency thereof. A mechanical spectroscopic device 112 ascertains the biomechanical properties of the cornea, for example on the basis of mechanical resonance. Partial vacuum is supplied to the eye-suction device via the supply device 110. Furthermore, a power supply is guaranteed with the supply device 110, and the measurement signals of the measuring means are transmitted to an evaluating device (not shown) via an electrical cable, a glass fibre and/or radio. On the applanation element 104 and on the eye-suction device 102 there may be provided contact elements, in order to transmit electrical signals and to provide a power supply.

On the retaining element 102 there are further provided position-measuring means 120, in order to determine the position of the eye-suction device 116 or of the retaining element 102 in space. The position-measuring means 120 may be, for example, acoustic or optical sensors, which determine the position in relation to a reference geometry. Furthermore, in the case of the position sensors 120 it may be a question of purely passive sensors which receive a beam radiated from a reference location, the position of the eye-suction device 116 or of the retaining element 102 being determined on the basis of the signal received. Similarly, the position-measuring means 120 may be purely active elements which emit an optical or acoustic beam which is received by a corresponding receiving device at a reference location, the position of the position-measuring means 120 in space being determined on the basis of the signal received. On the eye-suction device 102 there may also be arranged reference marks which are registered by a camera arranged in space. Similarly, optical sensors which register the position of the eye may be arranged in the interior of the eye-suction device. With the aid of the registered position of the eyes in relation to the eye-suction ring 102 and the position of the eye-suction ring in space registered via the position-measuring means 120, the position of the eye 122 in space can be determined.

The means for determining the position of the suction ring in space may be coupled with a position control (not shown) of a treatment couch or with a position control (not shown) of a laser system.

In operation the eye-suction device 116 touches the eye. In the eye-suction device 116 a force sensor 118 is integrated, in order to measure the force acting on the eye, from which the intraocular pressure can be determined. A plurality of force sensors 118 may be arranged in the eye-suction device 116. As a result, a force profile along the periphery of the contact element 116 can be created, as a result of which the corneal profile can be ascertained and accordingly the intraocular pressure can be ascertained more precisely.

The eye-suction device 116 or the retaining element 102 may further include a fourth suction region (not shown) which evacuates the region between the applanation element and the cornea, in order that the cornea of the eye 122 rests securely against the applanation element 104.

The eye-suction device 116 and the retaining element 102 may be integrally formed or may be non-positively or positively connected.

The present invention has the advantage that it creates a redundancy, since, on the one hand, the eye-suction device is sucked onto the eye and, on the other hand, a part of the cornea is sucked onto a functional element or onto an element arranged thereon. Furthermore, the invention has the advantage that before, during and/or after the operation the operating surgeon can simply exchange a functional element—for example, a lens, an applanation lens or a connection region for the optics of a laser system—without using a tool that is difficult to operate. The invention further has the advantage that no mechanical fastening elements are required for arranging the functional element, which contributes towards miniaturizing the eye-suction device and reducing the weight thereof. Since no mechanical fastening elements are required, the eye-suction device can be constructed from fewer components and more simply, as a result of which the operating surgeon is given a better view of the operating field, the eye-suction device is given a higher numerical aperture, and the risk of failure is reduced. Furthermore, the eye-suction device according to the invention permits higher manufacturing tolerances than those pertaining to the state of the art.

It will be understood that each of the suction regions can be divided up into a plurality of self-sufficient suction regions, as a result of which a further redundancy with enhanced safety arises.

The eye-suction device 116 and the retaining element 102 may be integrally formed or may be non-positively or positively connected.

The present invention has the advantage that it provides measurement data relating to the eye before, during and/or after an operation. The invention provides measurement data with respect to the intraocular pressure, the position of the suction ring in space, the mechanical force that is acting on an eye, measurement data relating to the cornea, for example the water content thereof, the biomechanical properties thereof and the transparency thereof. Furthermore, no additional measuring instruments have to be provided in order to monitor the eye during an operation.

The invention has been described by means of several embodiments. A person skilled in the art will understand that the features and feature combinations of the various embodiments may be combined.

The invention claimed is:

1. A device for eye surgery, the device configured to hold a fluid other than air between a focusing lens and a cornea of an eye during treatment of the eye, the device comprising: suction ring configured to be placed on an eye to be treated, the suction ring having a first suction region adjacent a first end of the suction ring, the first suction region configured to secure the suction ring against the eye through application of a vacuum to a first fluid pathway of the first suction region; and a container member coupled to the suction ring by applying a partial vacuum to a second fluid pathway of a second suction region of the suction ring adjacent a second end of the suction ring, opposite the first end of the suction ring, the container member having a longitudinal axis and an interior chamber for receiving the fluid, the container member including a wall extending from a first axial end of the container member adjacent to the suction ring to an opposite second axial end of the container member and extending around the longitudinal axis, the wall closing the container member laterally to define the interior chamber, wherein a first opening for supplying the fluid to the interior extends through the wall adjacent the first axial end of the container member and a second opening for venting the interior extends through the wall adjacent the second axial end of the container member, wherein the first and second openings are offset relative to one another along the longitudinal axis of the container member, and wherein the second axial end of the wall of the container member is configured to be coupled to the focusing lens of a laser system such that only the fluid is positioned between the focusing lens of the laser system and an outer surface of the eye when the interior chamber is filled with the fluid.

2. The device of claim 1, further comprising the focusing lens of the laser system.

3. The device of claim 1, further comprising the fluid for introduction into the interior chamber through the first opening.

4. The device of claim 3, wherein the fluid has a refractive index approximately equal to a refractive index of a cornea of the eye.

5. A method of treating an eye, comprising:
coupling a suction ring to the eye by applying a partial vacuum to a first fluid pathway of a first suction region of the suction ring adjacent a first end of the suction ring;
coupling a container element to the suction ring, wherein the container element includes a wall extending from a first axial end adjacent to the suction ring to an opposing second axial end such that the container element defines an interior chamber and wherein coupling the container element to the suction ring includes applying a partial vacuum to a second fluid pathway of a second suction region of the suction ring adjacent a second end of the suction ring, opposite the first end of the suction ring;
introducing a liquid into the interior chamber of the container element through a first opening in the wall of the container element adjacent the first axial end while removing air from the interior chamber through a second opening in the wall of the container element adjacent the second axial end to fill the interior chamber with the liquid, wherein the second axial end of the wall of the container element is coupled to a focusing lens of a laser system such that only the liquid is positioned between the focusing lens of the laser system and an outer surface of the eye when the interior chamber is filled with the liquid.

6. The method of claim 5, further comprising removing at least a portion of the liquid from the interior chamber through the second opening in the wall of the container element.

7. The method of claim 5, wherein the liquid introduced into the interior chamber of the container element has a refractive index approximately equal to a refractive index of a cornea of the eye.

8. The method of claim 5, further comprising cutting a portion of a cornea of the eye with laser radiation supplied by the laser system.

9. The method of claim 5, wherein applying the partial vacuum to the first fluid pathway of the first suction region of the suction ring utilizes a first partial-vacuum feed.

10. The method of claim 9, wherein applying the partial vacuum to the second fluid pathway of the second suction region of the suction ring utilizes a second partial-vacuum feed that is separate from the first-partial vacuum feed.

11. The method of claim 10, wherein the first partial-vacuum feed is connected to a first suction pump and the second partial-vacuum feed is connected to a second suction pump.

12. The method of claim 10, wherein the first partial-vacuum feed is connected to a suction pump via a first control valve and the second partial-vacuum feed is connected to the suction pump via a second control valve.

13. A method of treating an eye, comprising:
positioning a container element adjacent to a suction ring;
causing a partial vacuum to be applied to a first fluid pathway of the suction ring to securely couple a first end of the container element to a first end of the suction ring;
positioning the suction ring adjacent to the eye to be treated;
causing a partial vacuum to be applied to a second fluid pathway of the suction ring to securely couple a second end of the suction ring to the eye;
causing a liquid having a refractive index between about 1.35 and about 1.40 to be introduced into an interior chamber of the container element through a first opening in a sidewall of the container element adjacent the first end of the container element;
causing at least a portion of the liquid introduced into the interior chamber of the container element to be removed from the interior chamber through a second opening in the sidewall of the container element adjacent a second end of the container element, opposite the first end of the container element;
causing laser radiation to be directed onto the eye through a focusing lens of a laser system coupled to the second end of the container element, wherein only the liquid within the interior chamber of the container element is positioned between the focusing lens of the laser system and an outer surface of the eye.

14. The method of claim 13, wherein the partial vacuum applied to the first fluid pathway of the suction ring utilizes a first partial-vacuum feed and the partial vacuum applied to the second fluid pathway of the suction ring utilizes a second partial-vacuum feed that is separate from the first-partial vacuum feed.

* * * * *